(12) United States Patent
Fallin et al.

(10) Patent No.: US 9,615,932 B2
(45) Date of Patent: *Apr. 11, 2017

(54) PROSTHESIS FOR THE REPLACEMENT OF A POSTERIOR ELEMENT OF A VERTEBRA

(71) Applicant: GMEDELAWARE 2 LLC, Audubon, PA (US)

(72) Inventors: T. Wade Fallin, Hyde Park, UT (US); Robert W. Hoy, Essex Junction, VT (US); E. Marlowe Goble, Logan, UT (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/749,694

(22) Filed: Jun. 25, 2015

(65) Prior Publication Data

US 2015/0289987 A1 Oct. 15, 2015

Related U.S. Application Data

(63) Continuation of application No. 13/276,617, filed on Oct. 19, 2011, now Pat. No. 9,095,441, which is a continuation of application No. 12/328,964, filed on Dec. 5, 2008, now Pat. No. 8,066,741, which is a continuation of application No. 11/083,710, filed on Mar. 18, 2005, now Pat. No. 7,566,345, which is a continuation of application No. 10/196,716, filed on Jul. 16, 2002, now Pat. No. 6,902,580, which is a continuation of application No. 09/797,309, filed on Mar. 1, 2001, now Pat. No. 6,419,703, application No. 12/328,964, which is a continuation-in-part of application No. 11/456,509, filed on Jul. 10, 2006, now Pat. No. 7,618,455, which is a continuation of application No. 10/420,467, filed on Apr. 22, 2003, now Pat. No. 7,074,237, which is a continuation of (Continued)

(51) Int. Cl.
 A61F 2/44 (2006.01)
 A61B 17/86 (2006.01)
 A61F 2/30 (2006.01)

(52) U.S. Cl.
 CPC ............ *A61F 2/4405* (2013.01); *A61B 17/86* (2013.01); *A61B 2560/0443* (2013.01); *A61F 2002/30578* (2013.01); *A61F 2002/30604* (2013.01)

(58) Field of Classification Search
 CPC .......... A61F 2/4405; A61F 2002/30578; A61F 2002/30604; A61B 17/86; A61B 2560/0443
 USPC ...................... 623/17.11–17.16, 16.11, 18.11; 606/246–279
 See application file for complete search history.

(56) References Cited

U.S. PATENT DOCUMENTS 6,132,464 A * 10/2000 Martin ................... A61F 2/4405
 606/248
6,200,322 B1 * 3/2001 Branch .............. A61B 17/1757
 606/104

(Continued)

*Primary Examiner* — Pedro Philogene

(57) ABSTRACT

Prosthetic replacement for a posterior element of a vertebra comprising portions that replace the natural lamina and the four natural facets. The prosthetic replacement may also include portions that replace one or more of the natural spinous process and the two natural transverse processes. If desired, the prosthesis replacement may also replace the natural pedicles. A method for replacing a posterior element of a vertebra is also provided.

20 Claims, 19 Drawing Sheets

Related U.S. Application Data application No. 09/736,103, filed on Dec. 13, 2000, now Pat. No. 6,565,605.

(56) References Cited

U.S. PATENT DOCUMENTS

| | | | | |
|---|---|---|---|---|
| 6,419,703 B1* | 7/2002 | Fallin | ............... | A61F 2/4405 |
| | | | | 606/247 |
| 6,610,091 B1* | 8/2003 | Reiley | ............... | A61B 17/1671 |
| | | | | 606/246 |
| 6,902,580 B2* | 6/2005 | Fallin | ............... | A61F 2/4405 |
| | | | | 606/246 |
| 7,566,345 B1* | 7/2009 | Fallin | ............... | A61F 2/4405 |
| | | | | 606/248 |
| 8,066,741 B2* | 11/2011 | Fallin | ............... | A61F 2/4405 |
| | | | | 128/898 |
| 9,095,441 B2* | 8/2015 | Fallin | ............... | A61F 2/4405 |

* cited by examiner

PROSTHESIS FOR THE REPLACEMENT OF A POSTERIOR ELEMENT OF A VERTEBRA

CROSS-REFERENCE TO RELATED APPLICATIONS

This application is a continuation of U.S. application Ser. No. 13/276,617, filed Oct. 19, 2011, which is a continuation of U.S. application Ser. No. 12/328,964, filed on Dec. 5, 2008, now issued as U.S. Pat. No. 8,066,741, which is a continuation of U.S. application Ser. No. 11/083,710, filed Mar. 18, 2005, now issued as U.S. Pat. No. 7,566,345, which is a continuation of U.S. application Ser. No. 10/196,716, filed Jul. 16, 2002, now issued as U.S. Pat. No. 6,902,580, which is a continuation of U.S. application Ser. No. 09/797,309, filed Mar. 1, 2001, now issued as U.S. Pat. No. 6,419,703, U.S. Ser. No. 12/328,964, filed on Dec. 5, 2008, is also a continuation-in-part application of U.S. application Ser. No. 11/456,509, filed Jul. 10, 2006, now issued as U.S. Pat. No. 7,618,455, which is a continuation of U.S. application Ser. No. 10/420,467, filed Apr. 22, 2003, now issued as U.S. Pat. No. 7,074,237, which is a continuation of U.S. application Ser. No. 09/736,103, filed Dec. 13, 2000, now issued as U.S. Pat. No. 6,565,605.

All of the foregoing are incorporated herein by reference entirety.

BACKGROUND OF THE INVENTION

1. Field of the Invention

The present invention relates to surgical devices and methods in general, and more particularly to surgical devices and methods for restoring a damaged, diseased or otherwise painful spinal joint.

2. Description of Related Art

Traumatic, inflammatory, metabolic, synovial, neoplastic and degenerative disorders of the spine can produce debilitating pain that can have severe socioeconomic and psychological effects.

One of the most common surgical interventions today is arthrodesis, or spine fusion, in which two or more adjacent vertebral bodies are fused together in order to alleviate pain associated with the disc(s) located between those vertebral bodies. Approximately 300,000 such procedures are performed annually in the United States alone. Clinical success varies considerably, depending upon technique and indications, and consideration must be given to the concomitant risks and complications.

For example, while spine fusion generally helps to eliminate certain types of pain, it has also been shown to decrease function by limiting the range of motion for patients in flexion, extension, axial rotation and lateral bending. Furthermore, it is believed that spine fusion creates increased stresses on (and, therefore, accelerated degeneration of) adjacent non-fused motion segments. Additionally, pseudoarthrosis, resulting from an incomplete or ineffective fusion, may reduce or even totally eliminate the desired pain relief for the patient. Also, the fusion device(s) used to effect fusion, whether artificial or biological, may migrate out of the fusion site, thereby creating significant new problems for the patient.

Recently, several attempts have been made to recreate the natural biomechanics of the spine through the use of an artificial disc. Artificial discs are intended to restore articulation between vertebral bodies so as to recreate the full range of motion normally allowed by the elastic properties of the natural disc, which directly connects two opposed vertebral bodies. However, the artificial discs developed to date do not adequately address the mechanics of motion of the spinal column.

In addition to the foregoing, posterior elements called the facet joints help to support axial, torsional and shear loads that act on the spinal column. Furthermore, the facet joints are diarthroidal joints that provide both sliding articulation and load transmission features. However, the facet joints can also be a significant source of spinal disorders and, in many cases, debilitating pain. For example, a patient may suffer from arthritic facet joints, severe facet joint tropism or otherwise deformed facet joints, facet joint injuries, etc. There is currently a lack of good interventions for facet joint disorders. Facetectomy, or the removal of the facet joints, may provide some relief, but it is also believed to produce significant decreases in the stiffness of the spinal column (i.e., hypermobility) in all planes of motion: flexion and extension, lateral bending, and axial rotation. Furthermore, problems with the facet joints can also complicate treatments associated with other portions of the spine. By way of example, contraindications for artificial discs include arthritic facet joints, absent facet joints, severe facet joint tropism or otherwise deformed facet joints.

U.S. Pat. No. Re. 36,758 (Fitz) discloses an artificial facet joint where the inferior facet, the mating superior facet, or both, are covered with a cap. This cap requires no preparation of the bone or articular surfaces; it covers, and therefore preserves, the bony and articular structure.

The capping of the facet has several potential disadvantages, however. If the facet joint is osteoarthritic, a cap will not remove the source of the pain. Additionally, at least in the case of surface replacements for osteoarthritic femoral heads, the capping of articular bone ends has proven to lead to clinical failure by means of mechanical loosening. This clinical failure is hypothesized to be a sequela of disrupting the periosteum and ligamentum teres femoris, both serving a nutrition delivery role to the femoral head, thereby leading to avascular necrosis of the bony support structure for the surface replacement. It is possible that corresponding problems could develop from capping the facet. Another potential disadvantage of facet capping is that in order to accommodate the wide variability in anatomical morphology of the facets, not only between individuals but also between levels within the spinal column, a very wide range of cap sizes and shapes is required.

U.S. Pat. No. 6,132,464 (Martin) discloses a spinal facet joint prosthesis that is supported on the lamina (which is sometimes also referred to as the posterior arch). Extending from this support structure are inferior and/or superior blades that replace the cartilage at the facet joint. Like the design of the aforementioned U.S. Pat. No. Re. 36,758, the prosthesis of U.S. Pat. No. 6,132,464 generally preserves existing bony structures and therefore does not address pathologies which affect the bone of the facets in addition to affecting the associated cartilage. Furthermore, the prosthesis of U.S. Pat. No. 6,132,464 requires a secure mating between the prosthesis and the lamina. However, the lamina is a very complex and highly variable anatomical surface. As a result, in practice, it is very difficult to design a prosthesis that provides reproducible positioning against the lamina so as to correctly locate the cartilage-replacing blades for the facet joints.

Another approach to surgical intervention for spinal facets is disclosed in International Pat. Publication No. WO9848717A1 (Villaret et al.). While this publication teaches the replacement of spinal facets, the replacement is interlocked in a manner so as to immobilize the joint.

Thus it will be seen that previous attempts to provide facet joint replacement have proven inadequate.

In some circumstances, additional structures of a vertebra beside the facets may have been compromised by disease or trauma. For example, the lamina, the spinous process and/or the two transverse processes may have been compromised by disease or trauma. In such a circumstance, it would be useful to have a prosthesis which would allow the replacement of the same.

SUMMARY OF THE INVENTION

As a result, one object of the present invention is to provide a novel prosthesis tier the replacement of all four of the facets so as to remove the source of traumatic, arthritic or other disease-mediated pain.

Another object of the present invention is to provide a novel prosthesis for the replacement of different combinations of the posterior elements of a vertebra.

And another object of the present invention is to provide a novel prosthesis for the replacement of a posterior element of a vertebra that replicates the lamina, the four facets, the spinous process and the two transverse processes.

Still another object of the present invention is to provide a novel prosthesis for the replacement of a posterior element of a vertebra that replicates the lamina, the four facets and the spinous process.

Yet another object of the present invention is to provide a novel prosthesis for the replacement of a posterior element of a vertebra that replicates the lamina, the four facets and the two transverse processes.

Another object of the present invention is to provide a novel prosthesis for the replacement of a posterior element of a vertebra that replicates the lamina and the four facets.

And another object of the present invention is to provide a novel prosthesis for the replacement of a posterior element of a vertebra that replicates the two pedicles, the lamina, the four facets, the spinous process and the two transverse processes.

Still another object of the present invention is to provide a novel prosthesis for the replacement of a posterior element of a vertebra that replicates the two pedicles, the lamina, the four facets and the spinous process.

Yet another object of the present invention is to provide a novel prosthesis for the replacement of a posterior element of a vertebra that replicates the two pedicles, the lamina, the four facets and the two transverse processes.

Another object of the present invention is to provide a novel prosthesis for the replacement of a posterior element of a vertebra that replicates the two pedicles, the lamina and the four facets.

These and other objects are addressed by the present invention which, in one preferred embodiment, comprises a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; a pair of prosthetic inferior facets extending from the prosthetic lamina, a prosthetic spinous process extending from the prosthetic lamina; and a pair of prosthetic transverse processes extending from the two prosthetic mounts.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; a pair of prosthetic inferior facets extending from the prosthetic lamina; and a prosthetic spinous process extending from the prosthetic lamina.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; a pair of prosthetic inferior facets extending from the prosthetic lamina; and a pair of prosthetic transverse processes extending from the two prosthetic mounts.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic mounts; a prosthetic lamina extending from the two prosthetic mounts; a pair of prosthetic superior facets extending from the two prosthetic mounts and the prosthetic lamina; and a pair of prosthetic inferior facets extending from the prosthetic lamina.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; a pair of prosthetic inferior facets extending from the prosthetic lamina; a prosthetic spinous process extending from the prosthetic lamina; and a pair of prosthetic transverse processes extending from the two prosthetic pedicles.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; a pair of prosthetic inferior facets extending from the prosthetic lamina; and a prosthetic spinous process extending from the prosthetic lamina.

In another form of the invention, there is provided a prosthesis for the replacement of a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; a pair of prosthetic inferior facets extending from the prosthetic lamina; and a pair of prosthetic transverse processes extending from the two prosthetic pedicles.

In another form of the invention, there is provided a prosthesis for the replacement posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the prosthesis comprising a pair of prosthetic pedicles; a prosthetic lamina extending from the two prosthetic pedicles; a pair of prosthetic superior facets extending from the two prosthetic pedicles and the prosthetic lamina; and a pair of prosthetic inferior facets extending from the prosthetic lamina.

In another form of the invention, there is provided a method for replacing a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the two natural pedicles, the method comprising the steps of making a resection at the most dorsal aspect the two natural pedicles; and attaching a prosthesis to the resected vertebra, the prosthesis comprising a pair of prosthetic mounts, a prosthetic lamina extending from the two prosthetic mounts, a pair of prosthetic superior facets extending from the two prosthetic mounts and the prosthetic lamina, and a pair of prosthetic inferior facets extending from the prosthetic lamina.

In another form of the invention, there is provided a method for replacing a posterior element of a natural vertebra, wherein the natural vertebra comprises a natural vertebral body, a pair of natural pedicles extending from the natural vertebral body, a natural lamina extending from the two natural pedicles, a pair of natural superior facets extending from the two natural pedicles and the natural lamina, a pair of natural inferior facets extending from the natural lamina, a natural spinous process extending from the natural lamina, and a pair of natural transverse processes extending from the natural pedicles, the method comprising the steps of making a resection at the junction of the natural vertebral body and the two natural pedicles; and attaching a prosthesis to the resected vertebra, the prosthesis comprising a pair of prosthetic pedicles, a prosthetic lamina extending from the prosthetic pedicles, a pair of prosthetic superior facets extending from the two prosthetic pedicles and the prosthetic lamina, and a pair of prosthetic inferior facets extending from the prosthetic lamina.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein.

DETAILED DESCRIPTION OF THE PREFERRED EMBODIMENTS

Figure 1:
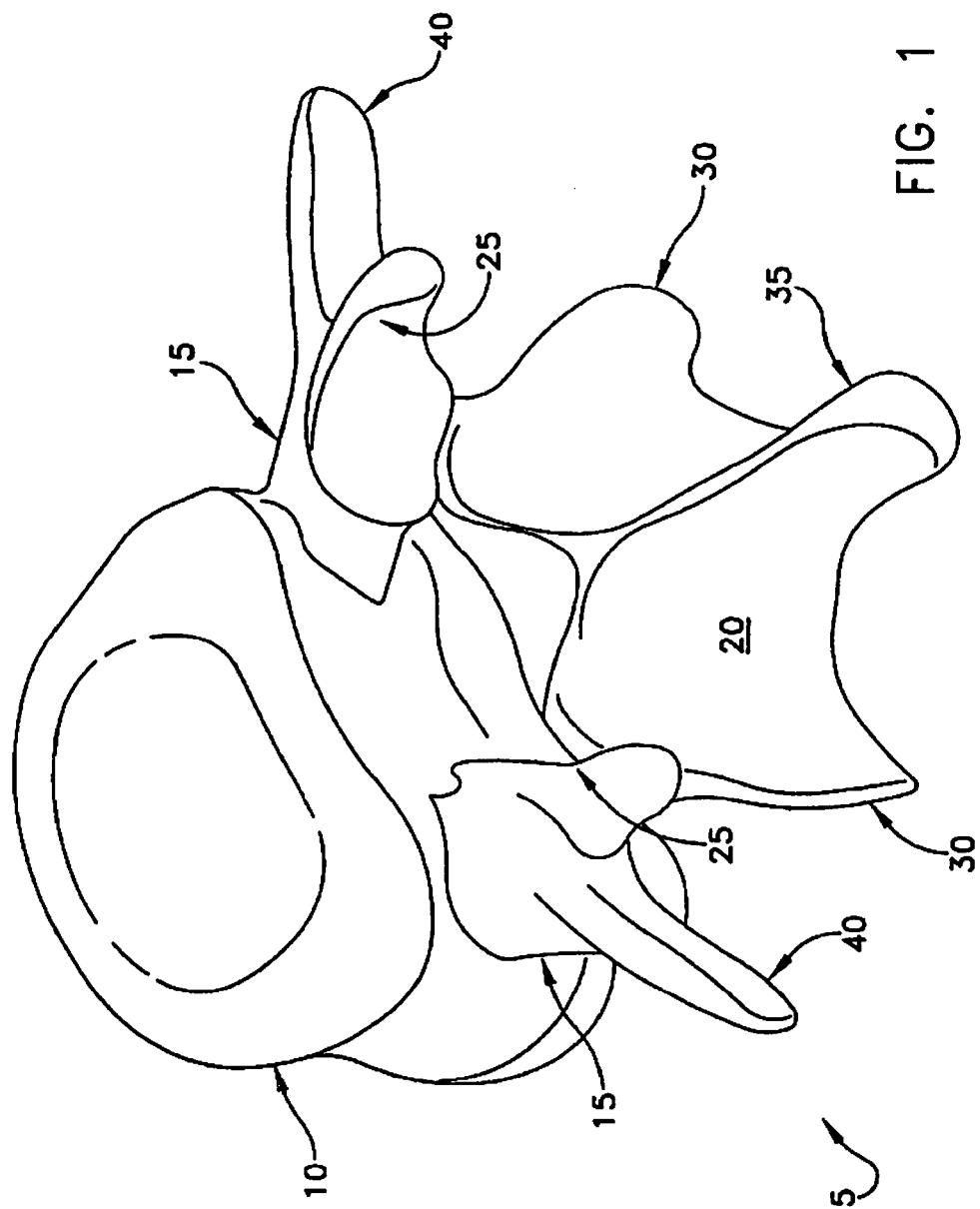
FIG. 1 is a perspective view of a lumbar vertebra.

Referring now to FIG. 1, there is shown a natural lumbar vertebra 5 comprising a natural vertebral body 10, a pair of natural pedicles 15 extending from natural vertebral body 10, a natural lamina 20 extending from natural pedicles 15, a pair of natural superior facets 25 extending from natural pedicles 15 and natural lamina 20, a pair of natural inferior facets 30 extending from natural lamina 20, a natural spinous process 35 extending from natural lamina 20, and a pair of natural transverse processes 40 extending from natural pedicles 15.

Figure 2:
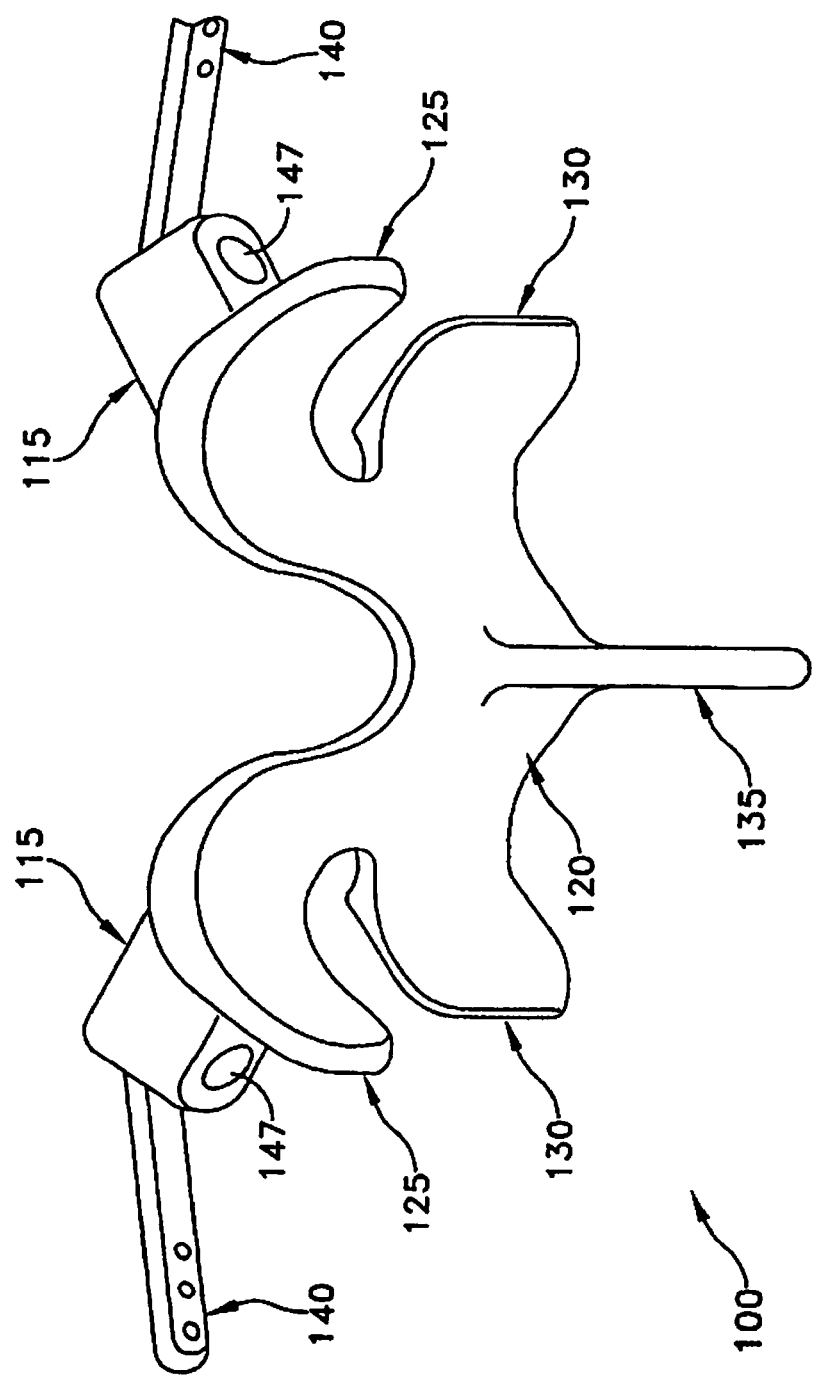
FIG. 2 is a perspective view of a novel prosthesis that replaces the lamina, the four facets, the spinous process and the two transverse processes of a vertebra.
Figure 3:
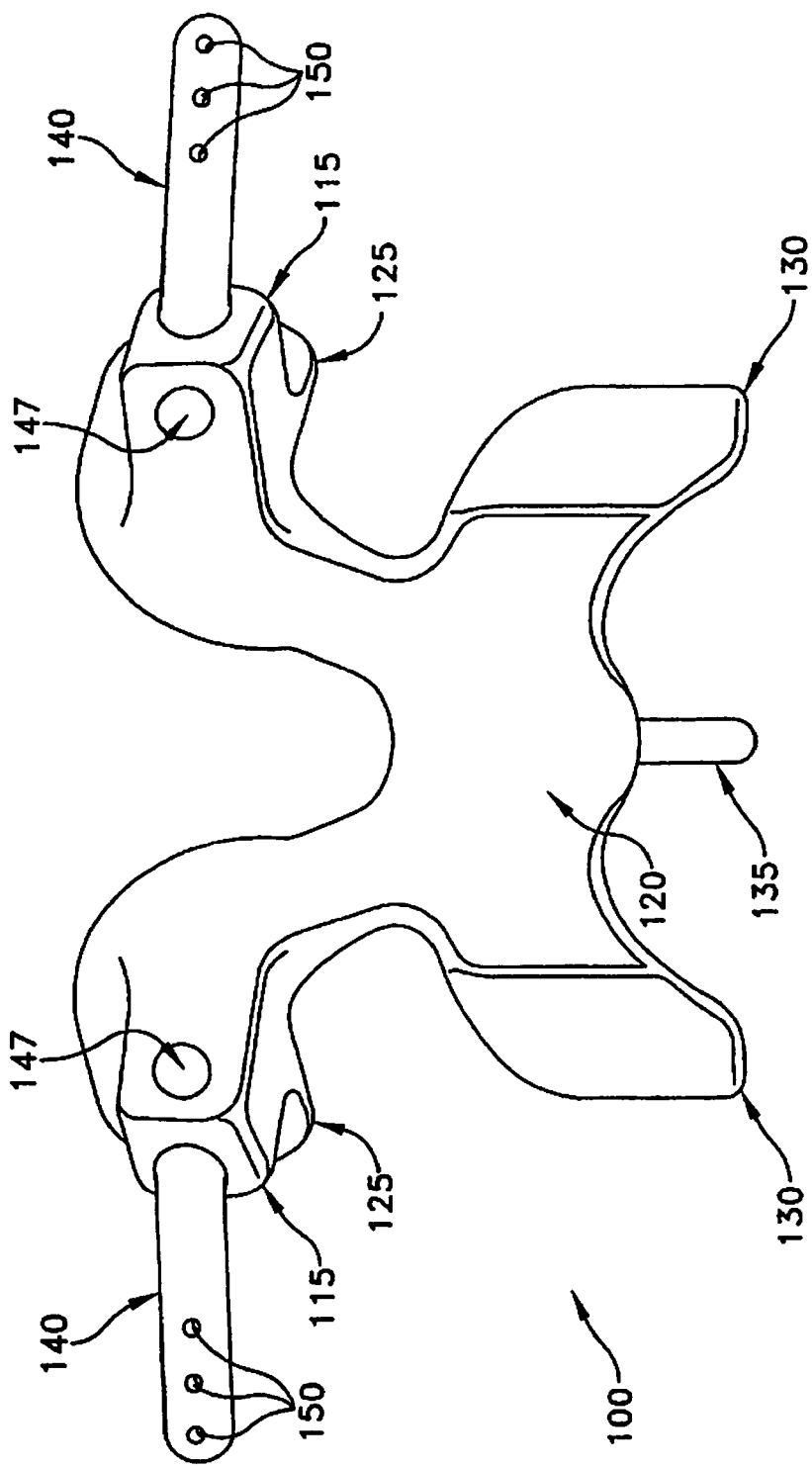
FIG. 3 is an anterior view of the prosthesis shown in FIG. 2.

Looking next at FIGS. 2 and 3, there is shown a novel prosthesis 100 which is adapted to replace the natural lamina 20, the two natural superior facets 25, the two natural inferior facets 30, the natural spinous process 35, and the two natural transverse processes 40. To this end, prosthesis 100 comprises a pair of prosthetic mounts 115, a prosthetic lamina 120 extending from prosthetic mounts 115, a pair of prosthetic superior facets 125 extending from prosthetic mounts 115 and prosthetic lamina 120, a pair of prosthetic inferior facets 130 extending from prosthetic lamina 120, a prosthetic spinous process 135 extending from prosthetic lamina 120, and a pair of prosthetic transverse processes 140 extending from prosthetic mounts 115.

Figure 4:
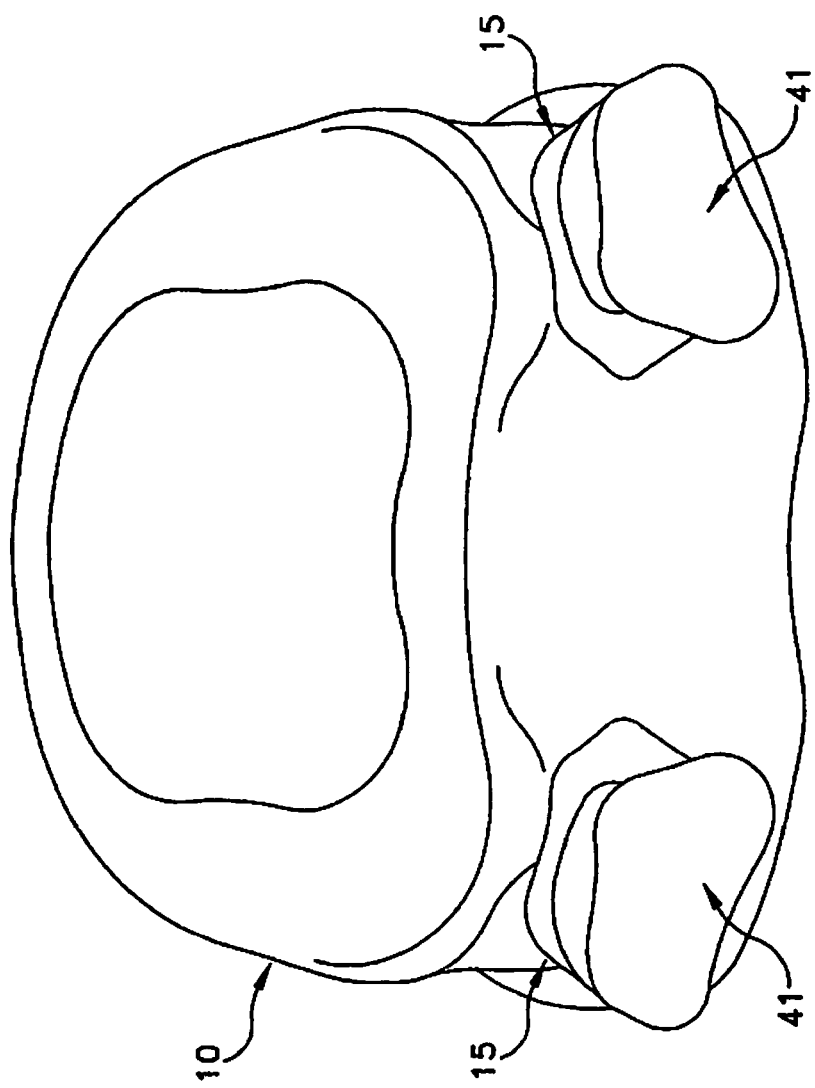
FIG. 4 is a perspective view of a vertebra which has been resected to receive the prosthesis shown in FIG. 2.
Figure 5:
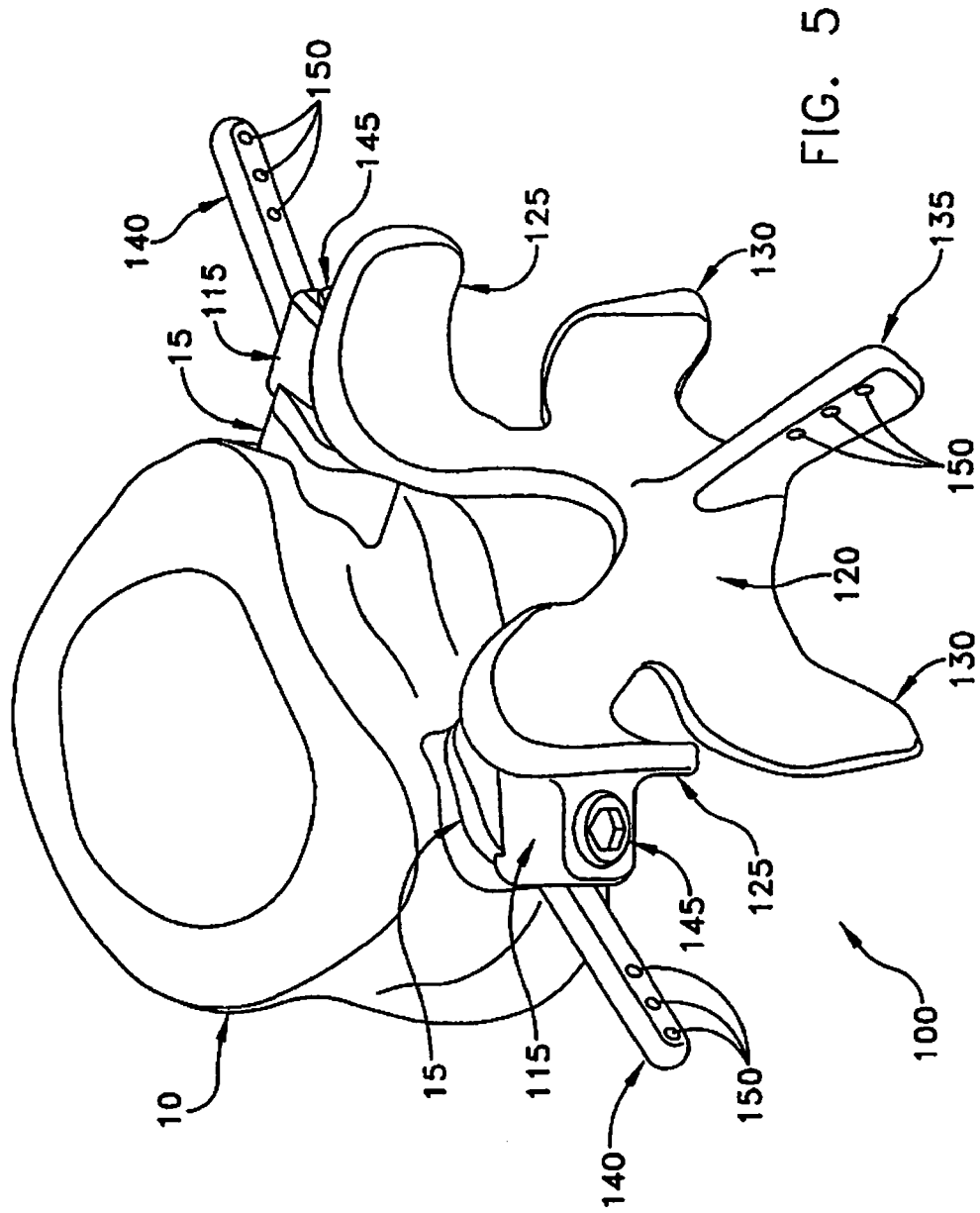
FIG. 5 is a perspective view of the prosthesis shown in FIG. 2 mounted to the resected vertebra shown in FIG. 4.
Figure 6:
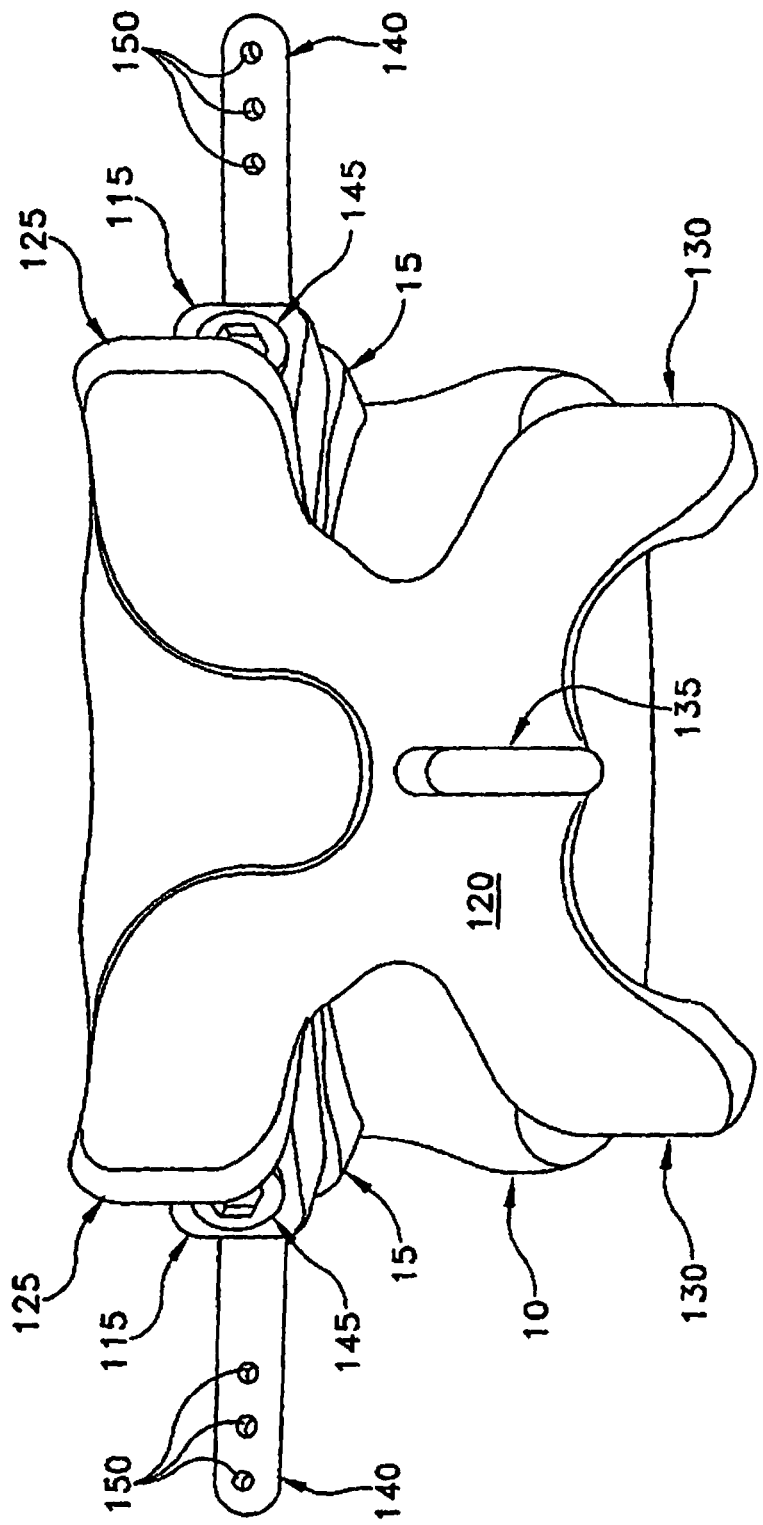
FIG. 6 is a dorsal view attic prosthesis shown in FIG. 2 mounted to the resected vertebra shown in FIG. 4.
Figure 7:
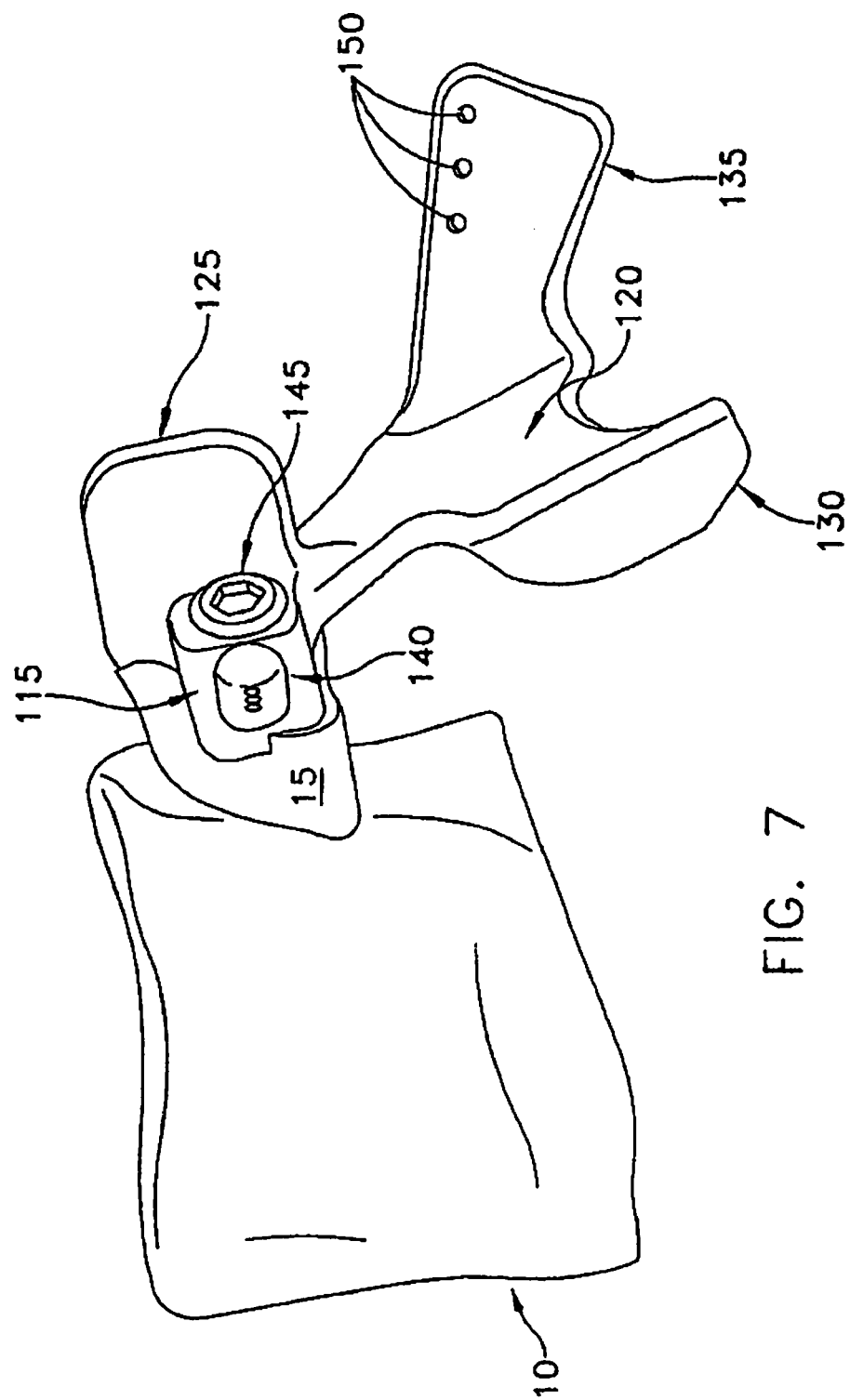
FIG. 7 is a lateral view of the prosthesis shown in FIG. 2 mounted to the resected vertebra shown in FIG. 4.

In the use of prosthesis 100, natural lumbar vertebra 5 is resected at its natural pedicles 15 so as to remove the natural lamina 20, the two natural superior facets 25, the two natural inferior facets 30, the natural spinous process 35, and the two natural transverse processes 40, leaving a pair of pedicle end surfaces 41 (FIG. 4). Then the prosthesis 100 may be attached to the natural pedicles 15, e.g., by placing prosthetic mounts 115 against pedicle surfaces 41 and then passing screws 145 through screw holes 147 and into natural pedicles 15, as shown in FIGS. 5-7. As seen in the drawings, the relative size, shape and positioning of the prosthetic lamina 120, the two prosthetic superior facets 125, the two prosthetic inferior facets 130, the prosthetic spinous process 135, and the two prosthetic transverse processes 140 essentially mimic the relative size, shape and positioning of the natural lamina 20, the two natural superior facets 25, the two natural inferior facets 30, the natural spinous process 35, and the two natural transverse processes 40, whereby to effectively restore the vertebra. If desired, holes 150 may be provided in the prosthetic spinous process 135 and/or the two prosthetic transverse processes 140 so as to facilitate re-attaching soft tissue to these structures.

Figure 8:
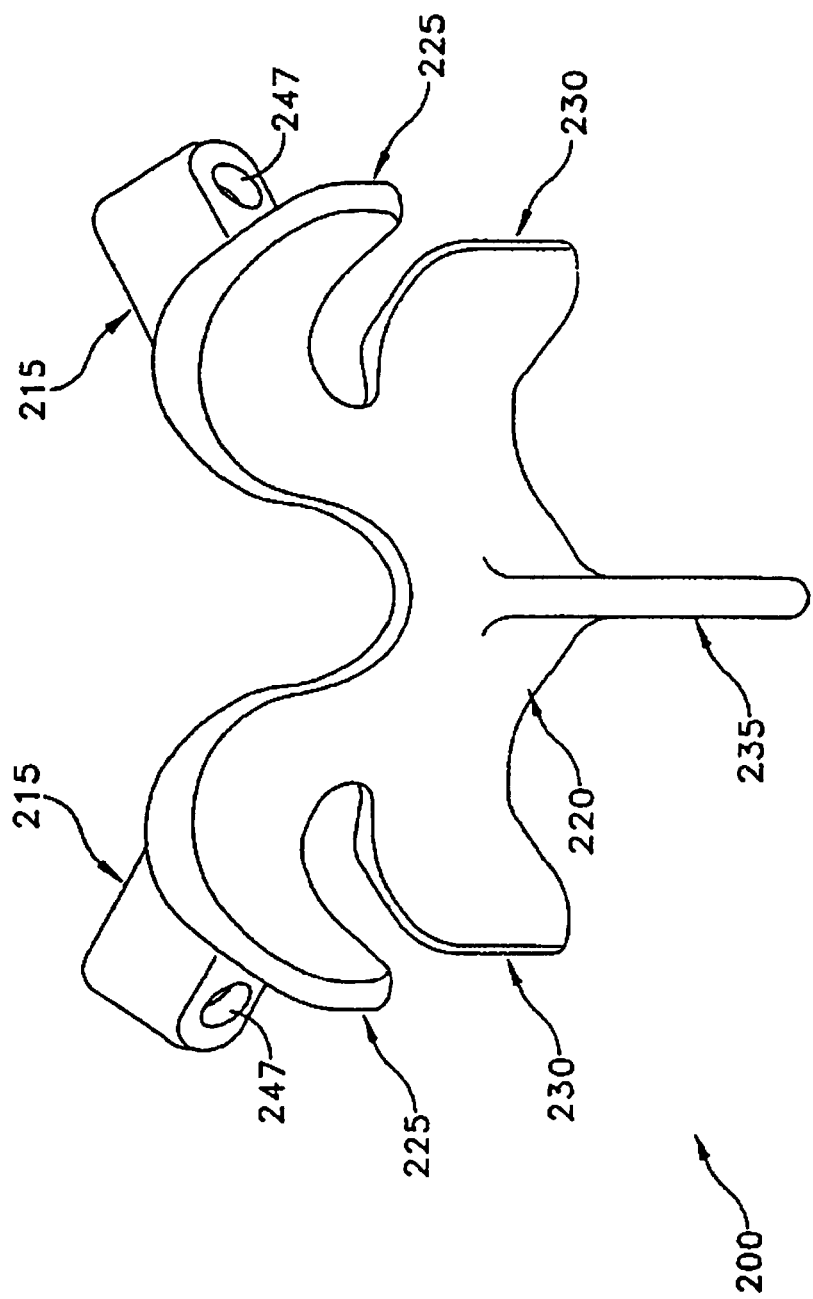
FIG. 8 is a perspective view of a novel prosthesis that replaces the lamina, the four facets and the spinous process of a vertebra.

Looking next at FIG. 8, there is shown a novel prosthesis 200 which is adapted to replace natural lamina 20, the two natural superior facets 25, the two natural inferior facets 30, and natural spinous process 35. To this end, prosthesis 200 comprises a pair of prosthetic mounts 215, a prosthetic lamina 220 extending from prosthetic mounts 215, a pair of prosthetic superior facets 225 extending from prosthetic mounts 215 and prosthetic lamina 220, a pair of prosthetic inferior facets 230 extending from prosthetic lamina 220, and a prosthetic spinous process 235 extending from prosthetic lamina 220.

In the use of prosthesis 200, natural lumbar vertebra 5 is resected at its natural pedicles 15 so as to remove the natural lamina 20, the two natural superior facets 25, the two natural inferior facets 30, the spinous process 35 and the two natural transverse processes 40, leaving a pair of pedicle surfaces 41 (FIG. 4). Then the prosthesis 200 may be attached to the natural pedicles 15, e.g., by placing prosthetic mounts 215 against pedicle surfaces 41 and then passing screws 145 through holes 247 and into natural pedicles 15. As seen in the drawing, the relative size, shape and positioning of prosthetic lamina 220, the two prosthetic superior facets 225, the two prosthetic interior facets 230, and the prosthetic spinous process 235 essentially mimic the relative size, shape and positioning of the natural lamina 20, the two natural superior facets 25 the two natural inferior facets 30, and the natural spinous process 35, whereby to effectively restore the vertebra. If desired, holes 150 may be provided in the prosthetic spinous process 235 so as to facilitate re-attaching soft tissue to this structure.

Figure 9:
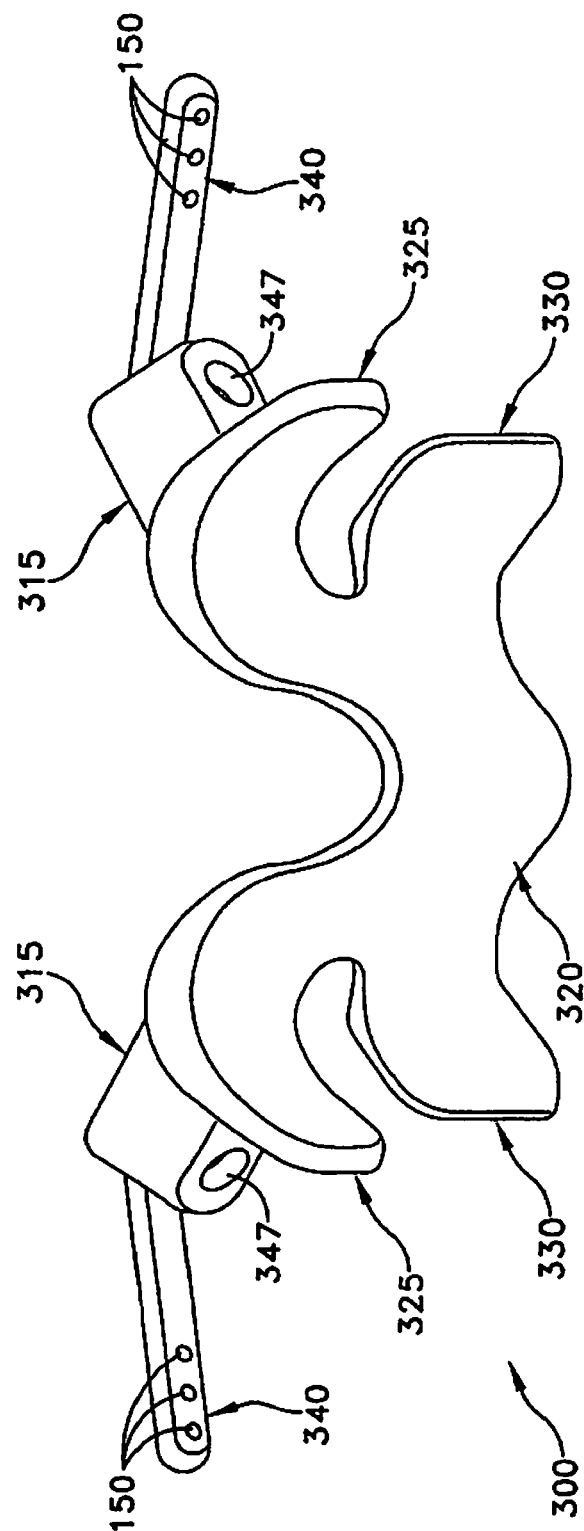
FIG. 9 is a perspective view of a novel prosthesis that replaces the lamina, the four facets and the two transverse processes of a vertebra.

Looking next at FIG. 9, there is shown a novel prosthesis 300 which is adapted to replace the natural lamina 20, the two natural superior facets 25, the two natural interior facets 30, and the two natural transverse processes 40. To this end, prosthesis 300 comprises a pair of prosthetic mounts 315, a prosthetic lamina 320 extending from prosthetic mounts 315, a pair of prosthetic superior facets 325 extending from prosthetic mounts 315 and prosthetic lamina 320, a pair of prosthetic inferior facets 330 extending from prosthetic lamina 320, and a pair of prosthetic transverse processes 340 extending from prosthetic mounts 315.

In the use of prosthesis 300, natural lumbar vertebra 5 is resected at natural pedicles 15 so as to remove natural lamina 20, the two natural superior facets 25, the two natural inferior facets 30, the natural spinous process 35 and the two natural transverse processes 40, leaving a pair of pedicle surfaces 41 (FIG. 4). Then the prosthesis 300 may be attached to the natural pedicles 15, e.g., by placing prosthetic mounts 315 against pedicle surfaces 41 and then passing screws 145 through holes 347 and into natural pedicles 15. As seen in the drawing, the relative size, shape and positioning of the prosthetic lamina 320, the two prosthetic superior facets 325, the two prosthetic inferior facets 330, and the two prosthetic transverse processes 340 essentially mimic the relative size, shape and positioning of the natural lamina 20, the two natural superior facets 25, the two natural inferior facets 30, and the two natural transverse processes 40, whereby to effectively restore the vertebra. If desired, holes 150 may be provided in the two prosthetic transverse processes 340 so as to facilitate re-attaching soft tissue to these structures.

Figure 10:
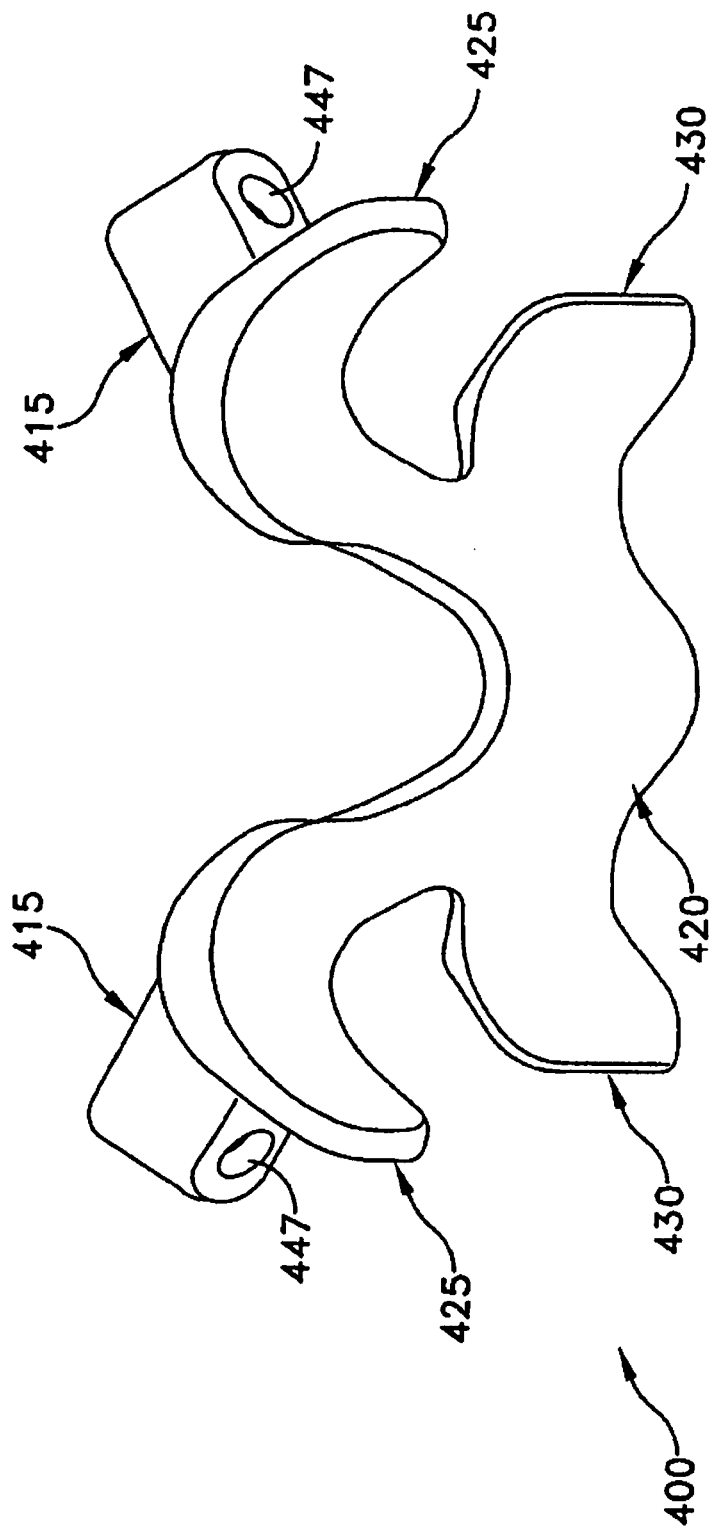
FIG. 10 is a perspective view of a novel prosthesis that replaces the lamina and the four facets of a vertebra.

Looking next at FIG. 10, there is shown a novel prosthesis 400 which is adapted to replace the natural lamina 20, the two natural superior facets 25, and the two natural inferior facets 30. To this end, prosthesis 400 comprises a pair of prosthetic mounts 415, a prosthetic lamina 420 extending from prosthetic mounts 415, a pair of prosthetic superior facets 425 extending from prosthetic mounts 415 and prosthetic lamina 420, and a pair of prosthetic inferior facets 430 extending from prosthetic lamina 420.

In the use of prosthesis 400, natural lumbar vertebra 5 is resected at pedicles 15 so as to remove the natural lamina 20, the two natural superior facets 25, the two natural inferior facets 30, the natural spinous process 35, and the two natural transverse processes 40, leaving a pair of pedicle surfaces 41 (FIG. 4). Then the prosthesis 400 may be attached to the natural pedicles 15, e.g., by placing prosthetic mounts 415 against pedicle surfaces 41 and then passing screws 145 through holes 447 and into natural pedicles 15. As seen in the drawing, the relative size, shape and positioning of prosthetic lamina 420, the two prosthetic superior facets 425, and the two prosthetic inferior facets 430 essentially mimic the relative size, shape and positioning of the natural lamina 20, the two natural superior facets 25 and the two natural inferior facets 30, whereby to effectively restore the vertebra.

Figure 11:
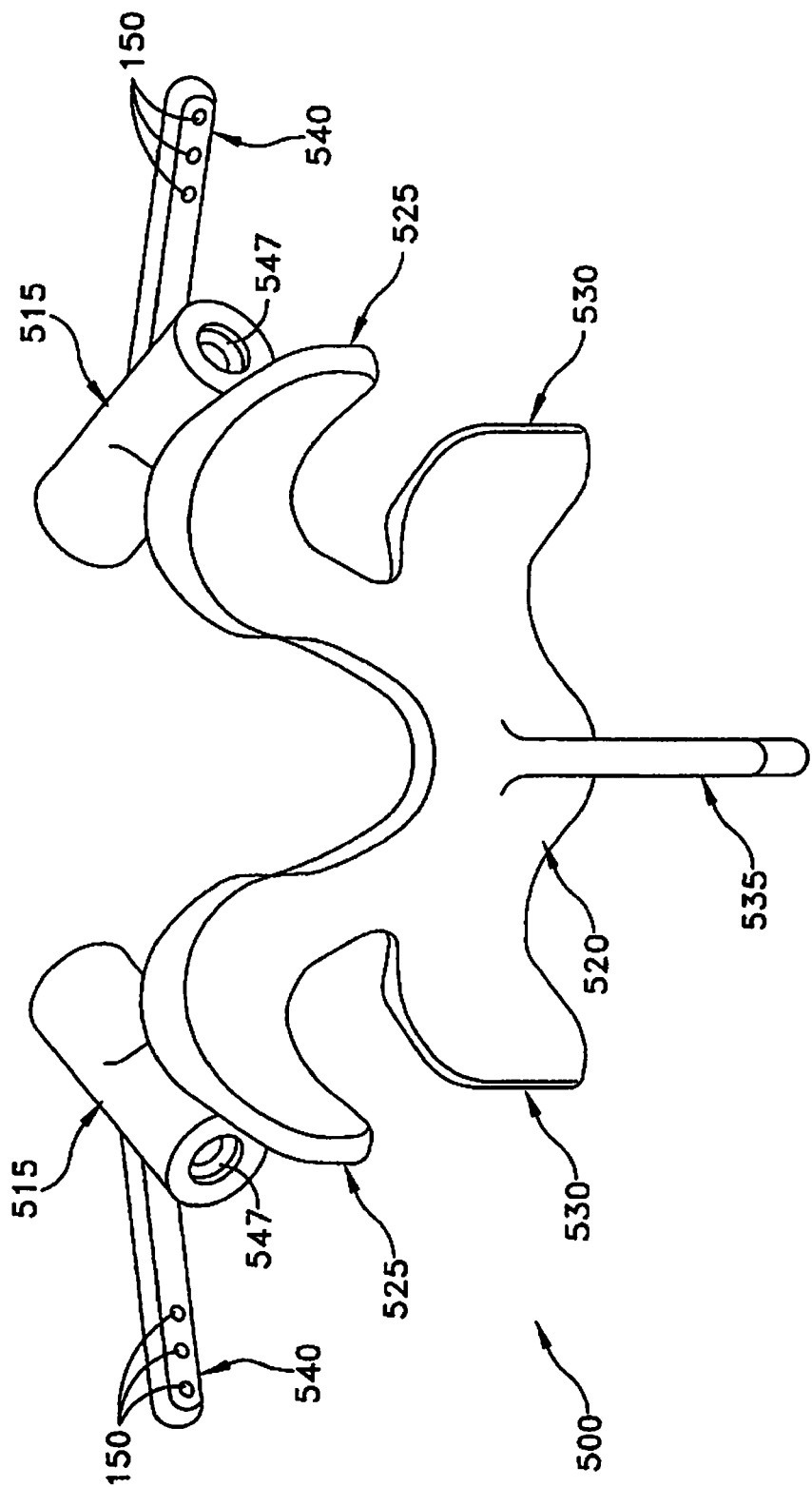
FIG. 11 is a perspective view of a novel prosthesis that replaces the two pedicles, the lamina, the four facets, the spinous process and the two transverse processes of a vertebra.
Figure 12:
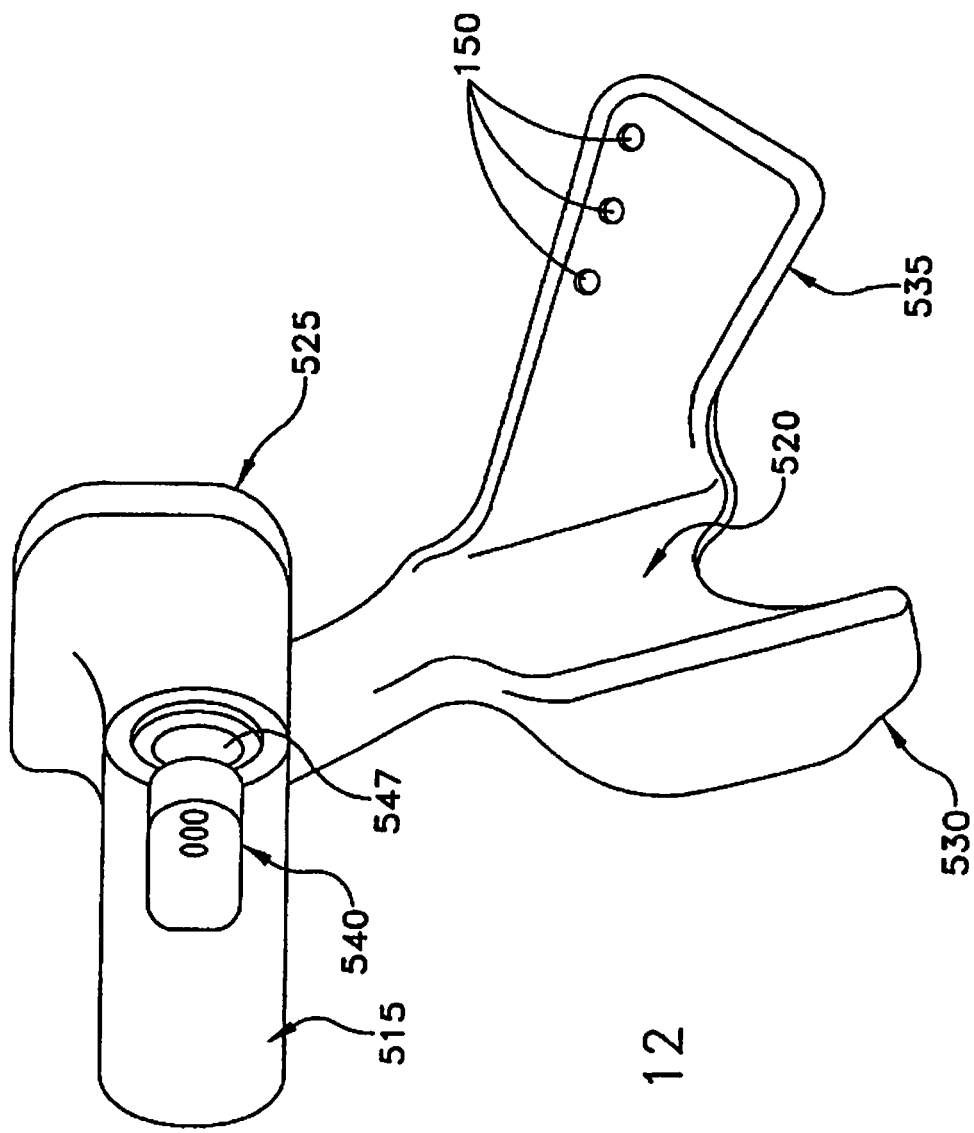
FIG. 12 is a lateral view of the prosthesis shown in FIG. 11.
Figure 13:
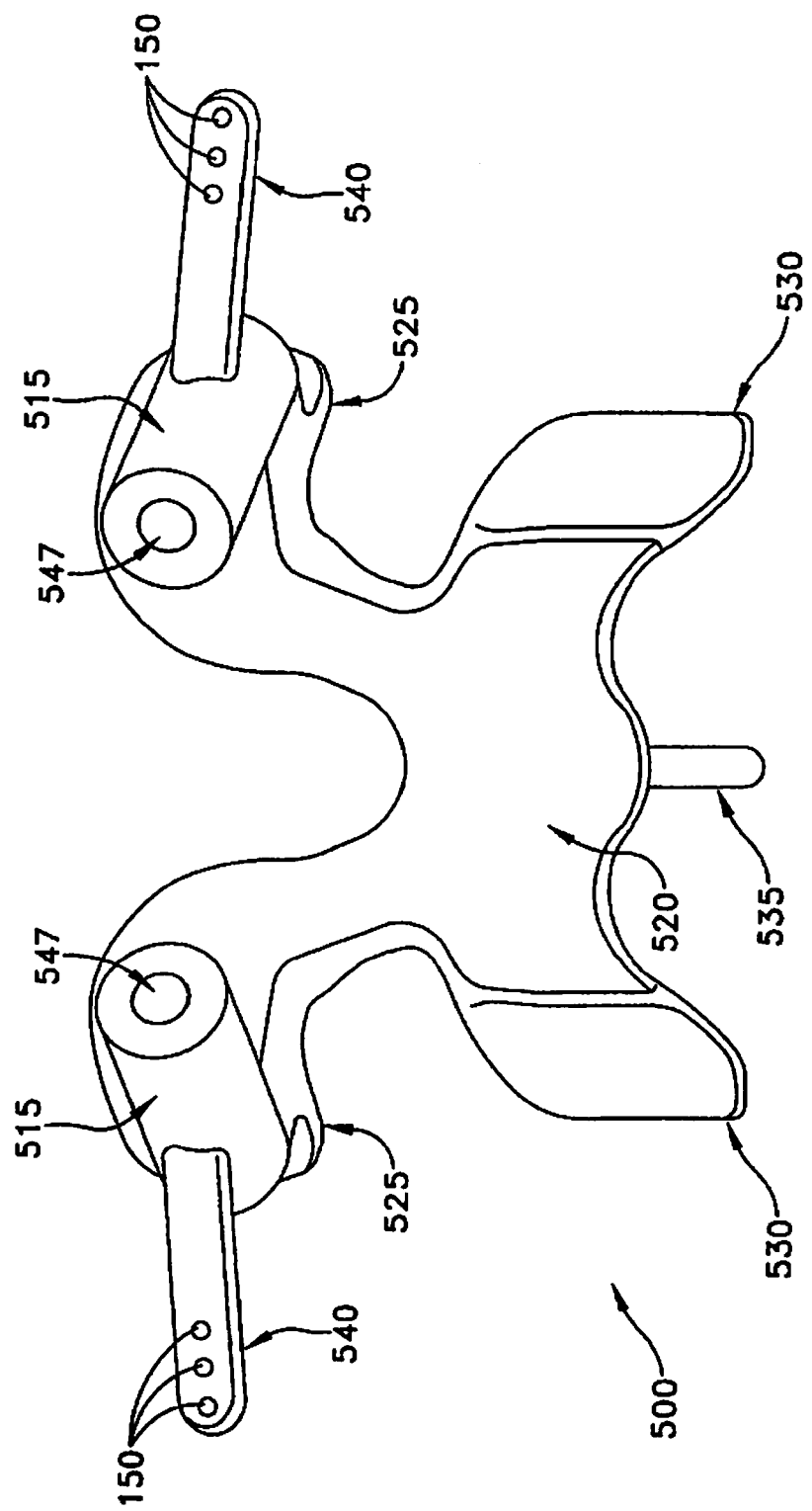
FIG. 13 is an anterior view of the prosthesis shown in FIG. 11.

Looking next at FIGS. 11-13, there is shown a novel prosthesis 500 which is adapted to replace a pair of natural pedicles 15, the natural lamina 20, the two natural superior facets 25, the two natural inferior facets 30, the natural spinous process 35, and the two natural transverse processes 40. To this end, prosthesis 500 comprises a pair of prosthetic pedicles 515, a prosthetic lamina 520 extending from prosthetic pedicles 515, a pair of prosthetic superior facets 525 extending from prosthetic pedicles 515 and prosthetic lamina 520, a pair of prosthetic inferior facets 530 extending from prosthetic lamina 520, a prosthetic spinous process 535 extending from prosthetic lamina 520, and a pair of prosthetic transverse processes 540 extending from prosthetic pedicles 515.

Figure 14:
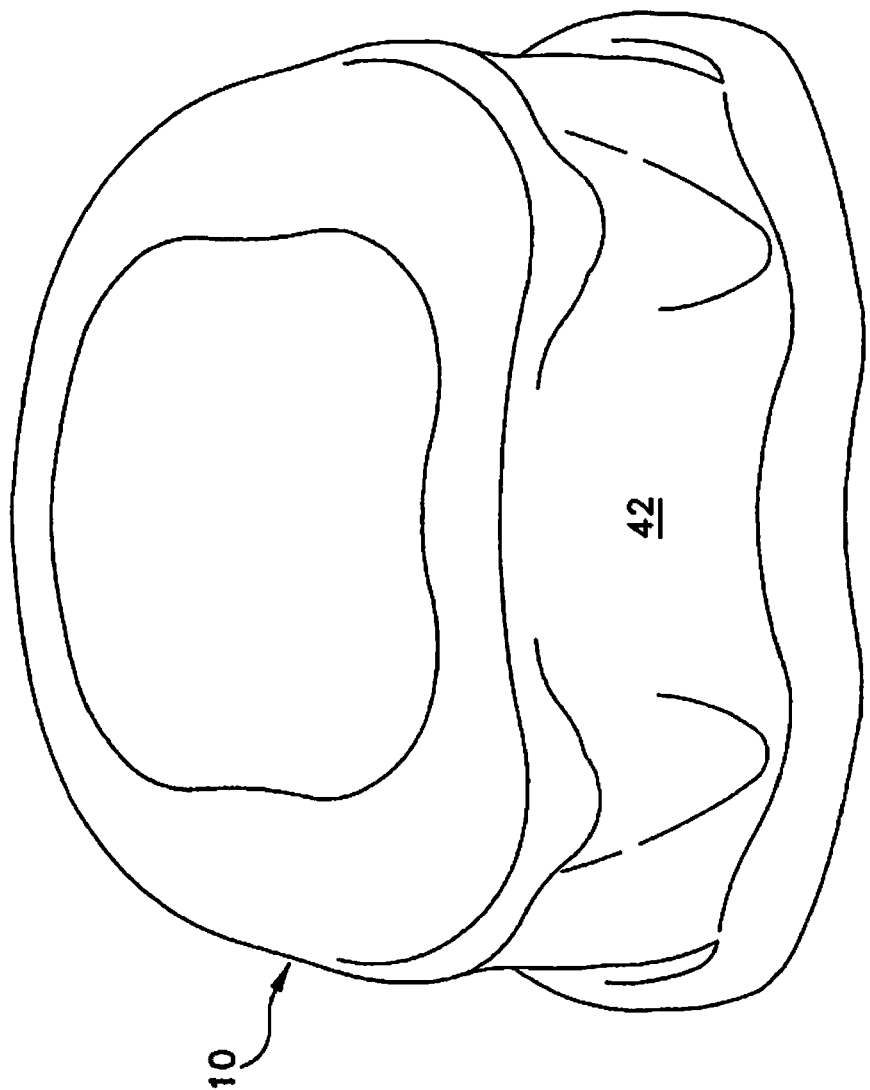
FIG. 14 is a perspective view of a vertebra which has been resected to receive the prosthesis shown in FIG. 11.
Figure 15:
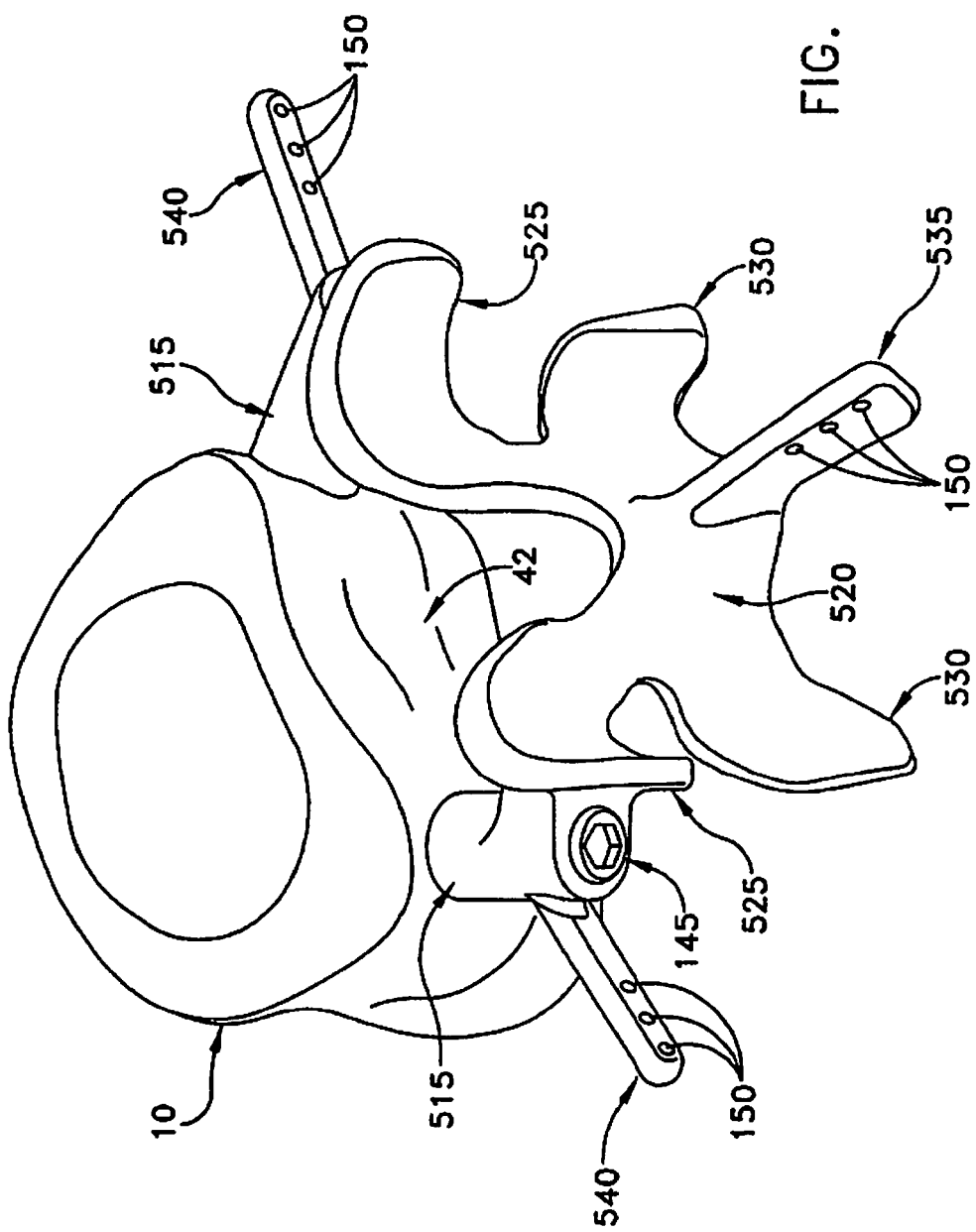
FIG. 15 is a perspective view showing the prosthesis of FIG. 11 mounted to the resected vertebra shown in FIG. 14.

In the use of prosthesis 500, natural lumbar vertebra 5 is resected at the bases of natural pedicles 15 so as to remove two natural pedicles 15, the natural lamina 20, the two natural superior facets 25, the two natural inferior facets 30, the natural spinous process 35, and the two natural transverse processes 40, leaving a vertebral body end face 42 (FIG. 14). Then the prosthesis 500 may be attached to the natural vertebral body 10, e.g., by placing prosthetic pedicles 515 against vertebral body end face 42 and then passing screws 145 through holes 547 and into natural vertebral body 10, as shown in FIG. 15. As seen in the drawings, the relative size, shape and positioning of the two prosthetic pedicles 515, the prosthetic lamina 520, the two prosthetic superior facets 525, the two prosthetic inferior facets 530, the prosthetic spinous process 535, and the two prosthetic transverse processes 540 essentially mimic the relative size, shape and positioning of the two natural pedicles 15, the natural lamina 20, the two natural superior facets 25, the two natural inferior facets 30, the natural spinous process 35, and the two natural transverse processes 40, whereby to effectively restore the vertebra. If desired, holes 150 may be provided in prosthetic spinous process 535 and the two prosthetic transverse processes 540 so as to facilitate re-attaching soft tissue to these structures.

Figure 16:
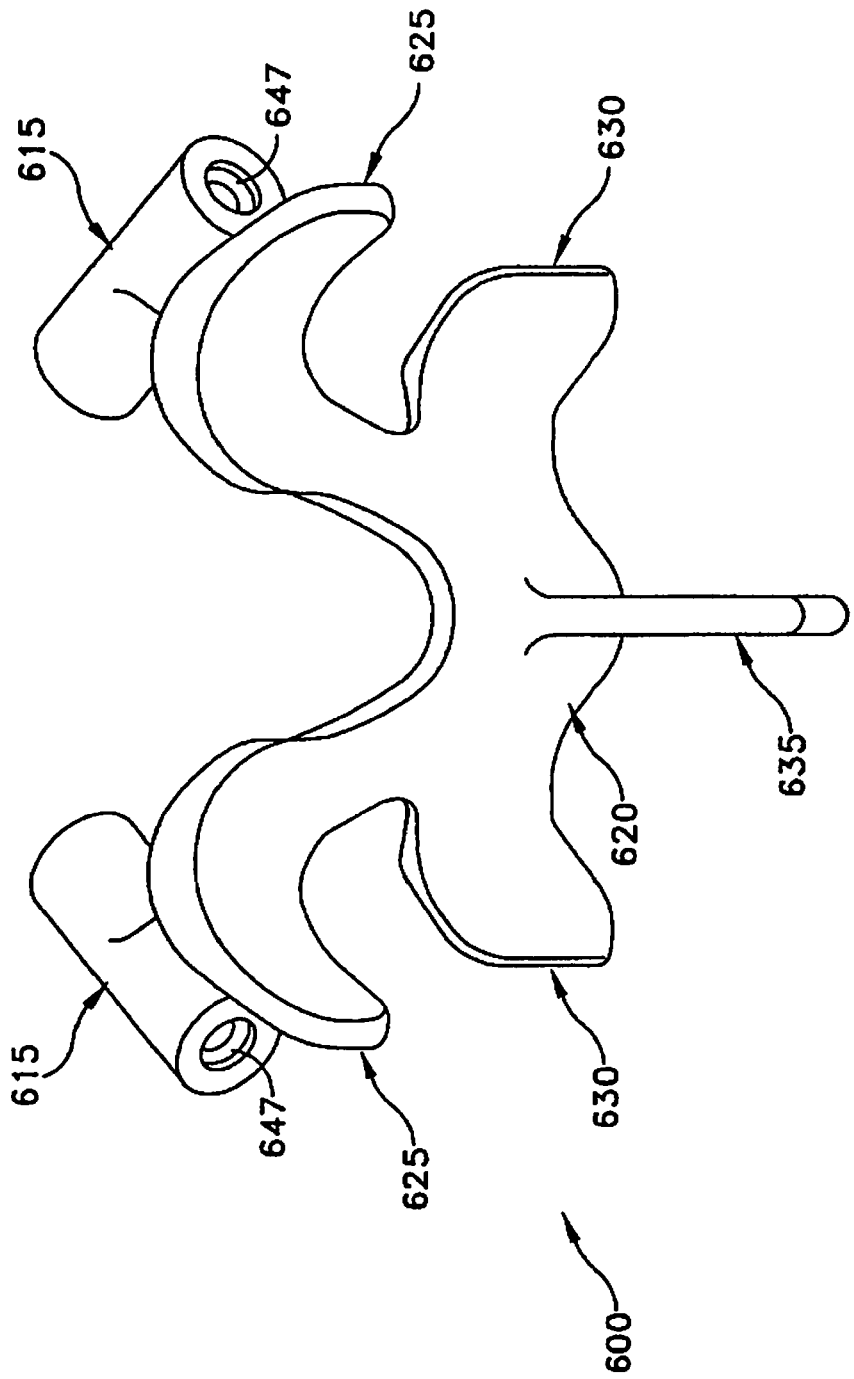
FIG. 16 is a perspective view of a novel prosthesis that replaces the two pedicles, the lamina, the four facets and the spinous process of a vertebra.
Figure 17:
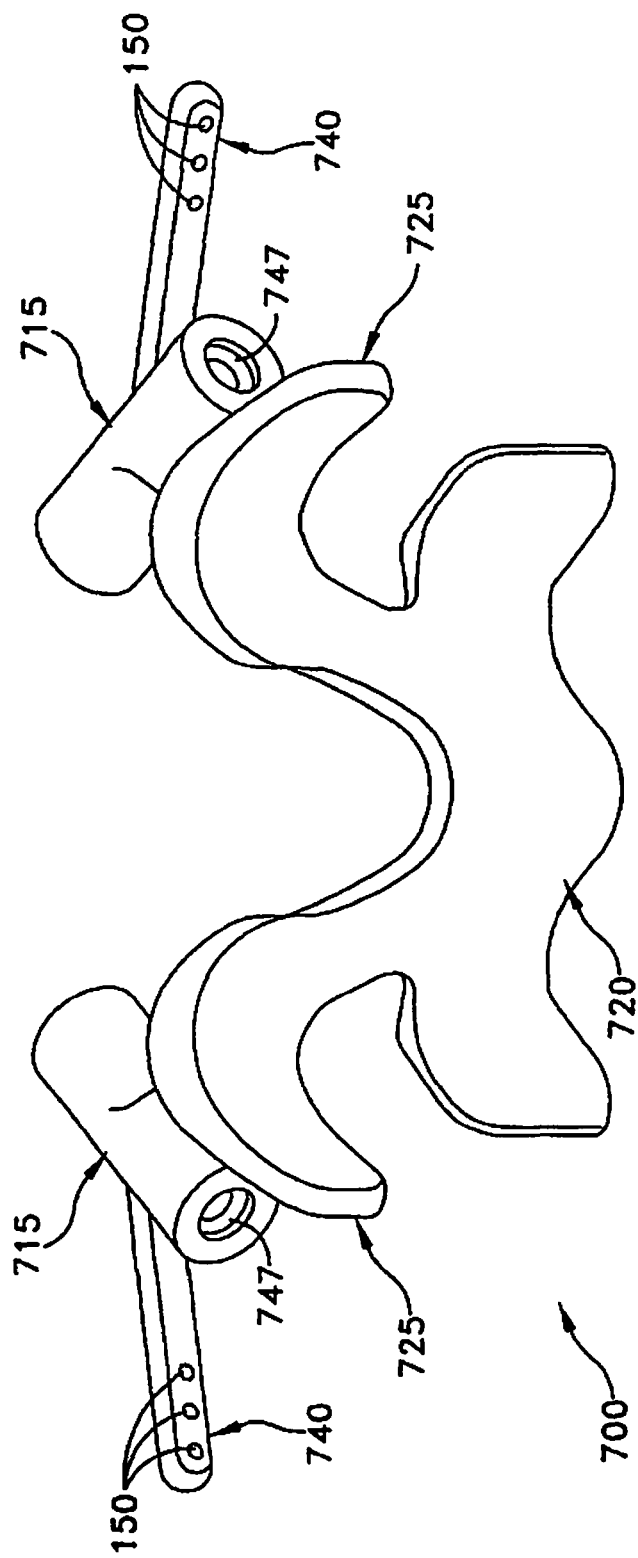
FIG. 17 is a perspective view of a novel prosthesis that replaces the two pedicles, the lamina, the four facets and the two transverse processes of a vertebra.

Looking next at FIG. 16, there is shown a novel prosthesis 600 which is adapted to replace the two natural pedicles 15, the natural lamina 20, the two natural superior facets 25, the two natural inferior facets 30, and the natural spinous process 35. To this end, prosthesis 600 comprises a pair of prosthetic pedicles 615, a prosthetic lamina 620 extending from prosthetic pedicles 615, a pair of prosthetic superior facets 625 extending from prosthetic pedicles 615 and prosthetic lamina 620, a pair of prosthetic inferior facets 630 extending from prosthetic lamina 620, and a prosthetic vinous process 635 extending from prosthetic lamina 620.

In the use of prosthesis 600, natural lumbar vertebra 5 is resected at the bases of natural pedicles 15 so as to remove the two natural pedicles 15, the natural lamina 20, the two natural superior facets 25, the two natural inferior facets 30, the natural spinous process 35 and the two natural transverse processes 40, leaving a vertebral body end face 42 (FIG. 14). Then the prosthesis 600 may be attached to the natural vertebral body 10, e.g., by placing prosthetic pedicles 615 against vertebral body end face 42 and then passing screws 145 through holes 647 and into natural vertebral body 10. As seen in the drawing, the relative size, shape and positioning of the two prosthetic pedicles 615, the prosthetic lamina 620, the two prosthetic superior facets 625, the two prosthetic inferior facets 630, and the prosthetic spinous process 635 essentially mimic the relative size, shape and positioning of the two natural pedicles 15, the natural lamina 20, the two natural superior facets 25, the two natural inferior facets 30, and the natural spinous process 35, whereby to effectively restore the vertebra. If desired, holes 150 may be provided in prosthetic spinous process 635 so as to facilitate re-attaching soft tissue to this structure.

Looking next at 17, there is shown a novel prosthesis 700 which is adapted to replace the two natural pedicles 15, the natural lamina 20, the two natural superior facets 25, the two natural inferior facets 30, and the two natural transverse processes 40. To this end, prosthesis 700 comprises a pair of prosthetic pedicles 715, a prosthetic lamina 720 extending from prosthetic pedicles 715, a pair of prosthetic superior facets 725 extending from prosthetic pedicles 715 and prosthetic lamina 720, a pair of prosthetic inferior facets 730 extending from prosthetic lamina 720, and a pair of prosthetic transverse processes 740 extending from prosthetic pedicles 715.

In the use of prosthesis 700, natural lumbar vertebra 5 is resected at the bases of natural pedicles 15 on as to remove the two natural pedicles 15, the natural lamina 20, the two natural superior facets 25, the two natural inferior facets 30, the natural spinous process 35, and the two natural transverse processes 40, leaving a vertebral body end face 42 (FIG. 14). Then the prosthesis 700 may be attached to the natural vertebral body 10, e.g., by placing prosthetic pedicles 715 against vertebral body end face 42 and then passing screws 145 through holes 747 and into vertebral body 10. As seen in the drawing, the relative size, shape and positioning of the two prosthetic pedicle 715, the prosthetic lamina 720, the two prosthetic superior facets 725, the two prosthetic interior facets 730, and the two prosthetic transverse processes 740 essentially mimic the relative size, shape and positioning of the two natural pedicles 15, the natural lamina 20, the two natural superior facets 25, the two natural inferior facets 30, and the two natural transverse processes 40, whereby to effectively restore the vertebra. If desired, holes 150 may be provided in the two prosthetic transverse processes 740 so as to facilitate re-attaching soft tissue to these structures.

Figure 18:
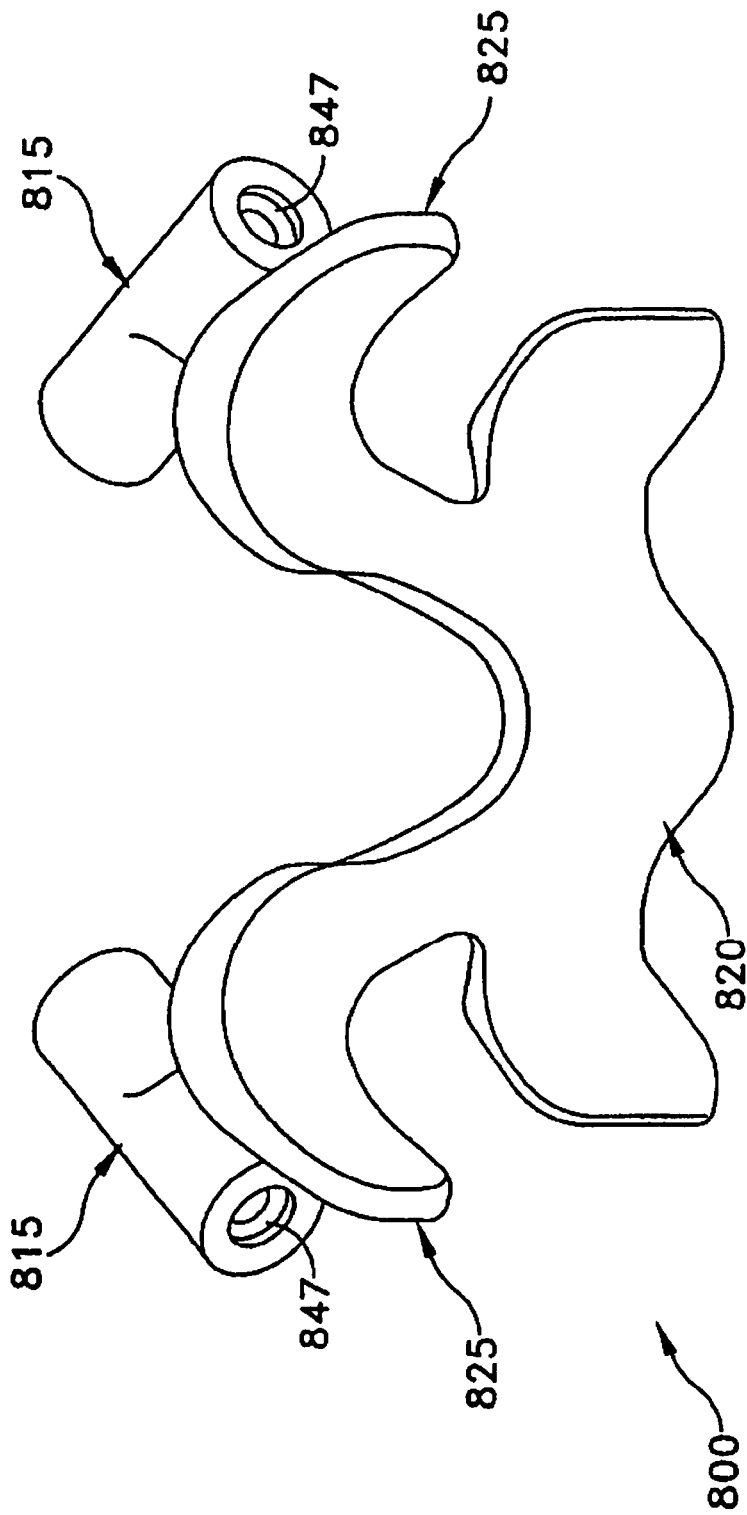
FIG. 18 is a perspective view of a novel prosthesis that replaces the two pedicles, the lamina and the four facets of a vertebra.

Looking next at FIG. 18, there is shown a novel prosthesis 800 which is adapted to replace the two natural pedicles 15, the natural lamina 20, the two natural superior facets 25, and the two natural inferior facets 30. To this end, prosthesis 800 comprises a pair of prosthetic pedicles 815, a prosthetic lamina 820 extending from prosthetic pedicles 815, a pair of prosthetic superior facets 825 extending from prosthetic pedicles 815 and prosthetic lamina 820, and a pair of prosthetic inferior facets 830 extending from prosthetic lamina 820.

In the use of prosthesis 800, natural lumbar vertebra 5 is resected at the bases of natural pedicles 15 on as to remove the two natural pedicles 15, the natural lamina 20, the two natural superior facets 25, the two natural inferior facets 30, the natural spinous process 35, and the two natural transverse processes 40, leaving a vertebral body end face 42 (FIG. 14). Then the prosthesis 800 may be attached to natural vertebral body 10, e.g., by placing prosthetic pedicles 715 against vertebral body end face 42 and then passing screws 145 through holes 847 and into natural vertebral body 10. As seen in the drawing, the relative size, shape and positioning of the two prosthetic pedicles 815, the prosthetic lamina 820, the two prosthetic superior facets 825, and the two prosthetic inferior facets 830 essentially mimic the relative size, shape and positioning of the two natural pedicles 15, the natural lamina 20, the two natural superior facets 25, and the two natural inferior facets 30, whereby to effectively restore the vertebra.

Figure 19:
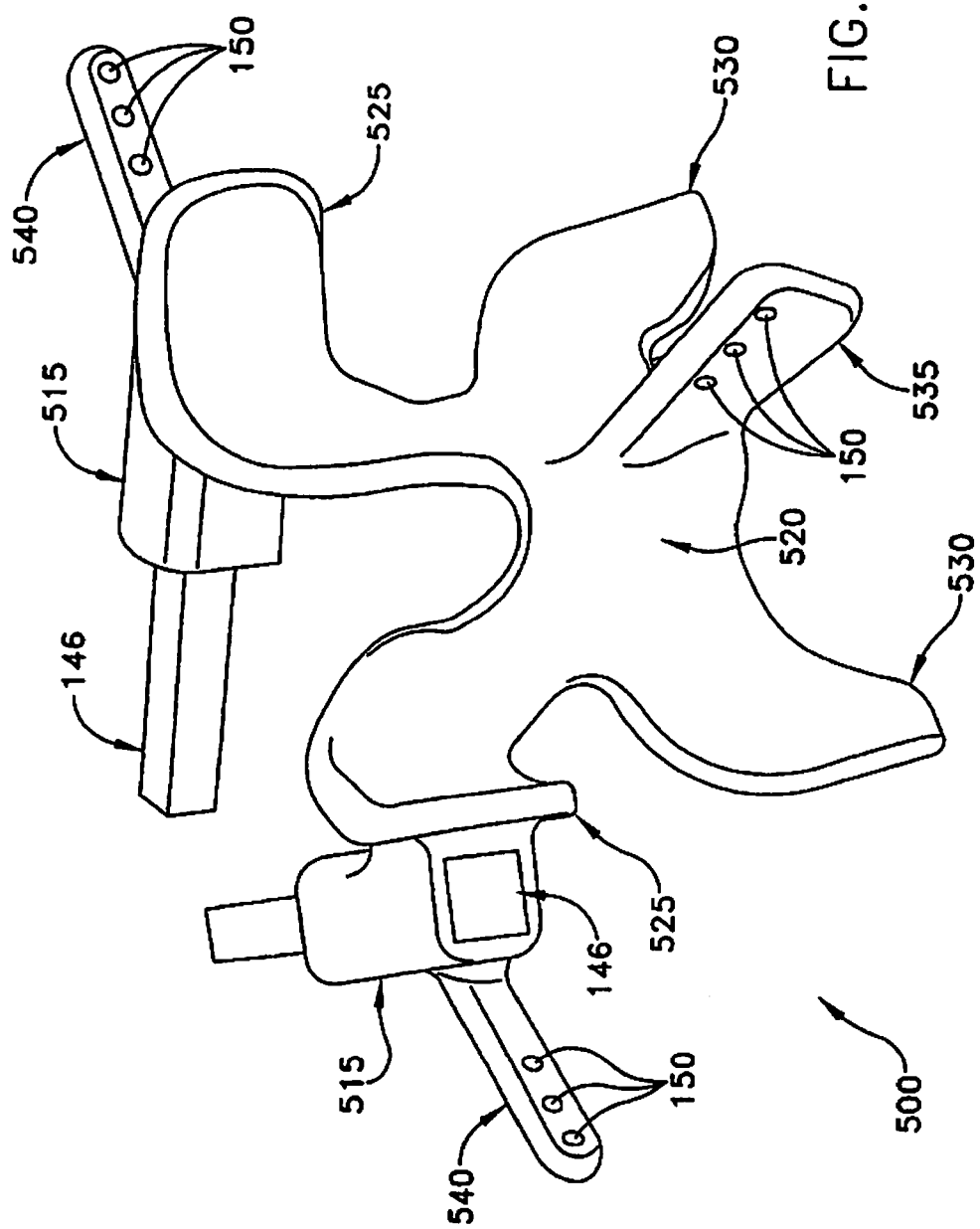
FIG. 19 is a perspective view showing an alternative arrangement for mounting the prosthesis of FIG. 1 to a vertebra.

It should also be appreciated that prostheses 100, 200, 300, 400, 500, 600, 700 and 800 may be attached to natural vertebra 5 with apparatus other than the screws 145 discussed above. Thus, for example, prostheses 100, 200, 300, 400, 500, 600, 700 and 800 may be attached to natural vertebra 5 with rods or posts, etc. See, for example, FIG. 19, where prosthesis 500 is shown attached to natural vertebra 5 with rods 146 which pass through, and snap into engagement with, prosthetic pedicles 515.

Having thus described preferred embodiments of the invention with reference to the accompanying drawings, it is to be understood that the embodiments shown herein are provided by way of example only, and that various changes and modifications may be effected by one skilled in the art without departing from the scope or spirit of the invention as defined in the claims.

What is claimed is:

1. A prosthetic implant comprising:
   a body portion configured to attach to a vertebral body, the body portion comprising a left upper portion, a right upper portion, a left lower portion and a right lower portion, wherein a first recess is formed between the left upper portion and the left lower portion and a second recess is formed between the right upper portion and the right lower portion;
   a first mount attached to the left upper portion, wherein the first mount includes a first screw hole that does not extend through the body portion; and
   a second mount attached to the right upper portion, wherein the second mount includes a second screw hole that does not extend through the body portion.

2. The implant of claim 1, wherein the left upper portion and the right upper portion each comprise a prosthetic superior facet.

3. The implant of claim 2, wherein the left lower portion and the right lower portion each comprise a prosthetic inferior facet.

4. The implant of claim 3, wherein a left prosthetic laminar is positioned adjacent the left lower portion and a right prosthetic laminar is positioned adjacent the right tower portion.

5. The implant of claim 4, wherein a prosthetic spinous process is positioned between the left prosthetic lamina and the right prosthetic lamina.

6. The implant of claim 1, wherein the first screw hole receives a first pedicle screw and the second screw hole receives a second pedicle screw.

7. The implant of claim 6, wherein the left upper portion and the right upper portion each comprise a prosthetic superior facet.

8. The implant of claim 7, wherein the left lower portion and the right lower portion each comprise a prosthetic inferior facet.

9. The implant of claim 8, wherein the body portion is a unitary body, wherein the unitary body further comprises a prosthetic spinous process.

10. The implant of claim 6, further comprising a first prosthetic transverse process that extends from the first mount and a second prosthetic transverse process that extends from the second mount.

11. The implant of claim 10, wherein the first prosthetic transverse process and the second prosthetic transverse process each comprise one or more holes.

12. A prosthetic implant comprising:
    a body portion configured to attach to a vertebral body, the body portion comprising a left upper portion, a right upper portion, a left lower portion and a right lower portion, wherein a first recess is formed between the left upper portion and the left lower portion and a second recess is formed between the right upper portion and the right lower portion;
    a first mount attached to the left upper portion, wherein the first mount includes a first screw hole that does not extend through the body portion;
    a second mount attached to the right upper portion, wherein the second mount includes a second screw hole that does not extend through the body portion;
    a first screw member received through the first screw hole of the first mount; and
    a second member received through the second screw hole of the second mount.

13. The implant of claim 12, wherein the first screw member and the second screw member are pedicle screws.

14. The implant of claim 12, wherein the body portion has a curved upper surface.

15. The implant of claim 12, wherein the left upper portion comprises a left prosthetic superior facet and the right upper portion comprises a right prosthetic superior facet.

16. The implant of claim 12, wherein the body portion is a unitary body that further comprises a prosthetic spinous process.

17. The implant of claim 16, further comprising a first prosthetic transverse process and a second prosthetic transverse process.

18. The implant of claim 17, wherein each of the first prosthetic transverse process and the second transverse process comprise a plurality of holes.

19. The implant of claim 12, wherein the left lower portion comprises a left prosthetic inferior facet and the right lower portion comprises a right prosthetic inferior facet, wherein the left prosthetic inferior facet is adjacent a left prosthetic lamina and the right prosthetic inferior facet is adjacent a right prosthetic lamina.

20. The implant of claim 19, wherein the left prosthetic lamina and the right prosthetic lamina each transition into opposing sides of a prosthetic spinous process.

\* \* \* \* \*